United States Patent [19]

Wilson

[11] Patent Number: 5,074,314
[45] Date of Patent: Dec. 24, 1991

[54] HEALTH CARE DEVICE

[76] Inventor: Frederick G. Wilson, 49 Hillsborough Old Road, Lisburn, County Antrim, Ireland

[21] Appl. No.: 511,988

[22] Filed: Apr. 13, 1990

Related U.S. Application Data

[63] Continuation of Ser. No. 129,736, Dec. 7, 1987, abandoned.

[30] Foreign Application Priority Data

Dec. 12, 1986 [GB] United Kingdom ................. 8629808

[51] Int. Cl.⁵ ............................ A61F 6/04; A61F 5/44
[52] U.S. Cl. ..................................... 128/844; 604/349
[58] Field of Search ....................... 604/349, 347, 351; 128/844, 842, 883, 884

[56] References Cited

U.S. PATENT DOCUMENTS

| D. 246,118 | 10/1977 | Okamoto | 604/349 |
|---|---|---|---|
| 2,410,460 | 11/1946 | Robinson | 128/844 |
| 2,567,926 | 9/1951 | Dunkelberger | 128/844 |
| 2,904,041 | 9/1959 | Brown | 128/844 |
| 3,282,414 | 11/1966 | Penksa | 128/844 |
| 3,951,141 | 4/1976 | Kopelowicz | 604/351 |
| 4,004,591 | 1/1977 | Freimark | 604/330 |
| 4,281,648 | 8/1981 | Rogers | 128/844 |
| 4,432,357 | 2/1984 | Pomeranz | 604/349 |
| 4,726,359 | 2/1988 | Schroeder | 128/844 |
| 4,840,187 | 6/1989 | Brazier | 128/844 |
| 4,869,241 | 9/1989 | Friedmann | 128/842 |
| 4,873,996 | 10/1989 | Maurer | 128/844 |
| 4,972,849 | 11/1990 | Park et al. | 128/842 |

FOREIGN PATENT DOCUMENTS

| 211350 | 6/1909 | Australia | 604/349 |
|---|---|---|---|
| 93307 | 2/1959 | Norway | 128/844 |
| 86/05681 | 10/1986 | PCT Int'l Appl. | 604/349 |
| 1250553 | 10/1971 | United Kingdom . | |

OTHER PUBLICATIONS

A New Method for the Profession, The Gee Bee Company, 8-23-34, pp. 11-15.
"Outline for Successful Prophylactic Program", The Gee Bee Co., 184 West Main St., Waterbury, Conn., pp. 13-15.

Primary Examiner—Randy Citrin Shay
Assistant Examiner—R. Clarke
Attorney, Agent, or Firm—Mason, Fenwick & Lawrence

[57] ABSTRACT

A health device comprising a sheath (10) having an annular ring (13) of solid but relatively pliable construction attached to the outward open end (11) thereof. The sheath (10) is formed to be inserted within a vaginal or anal body orifice prior to sexual intercourse. The annular ring (13) may be formed so as to be removeably attached to said sheath (10). The sheath (10) may be formed at its closed end (12) so as to encompass a formed shape (14, 15) to locate and maintain the sheath (10) in the body orifice during use.

14 Claims, 2 Drawing Sheets

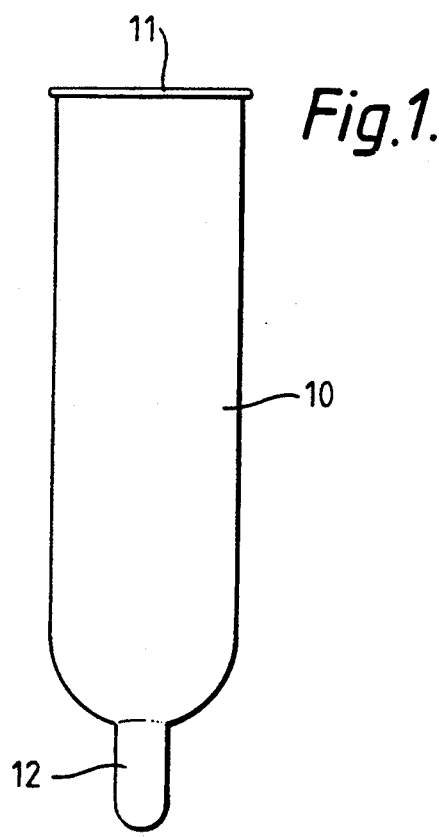
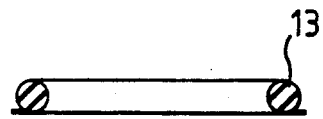
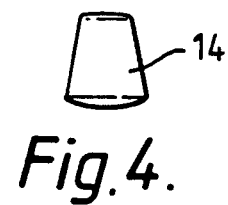
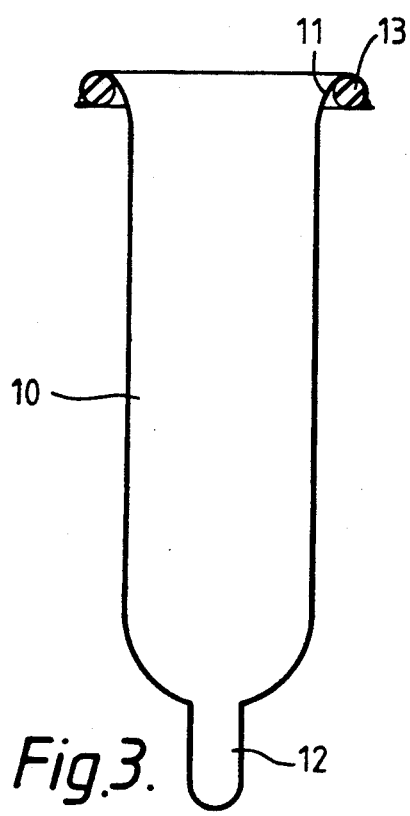
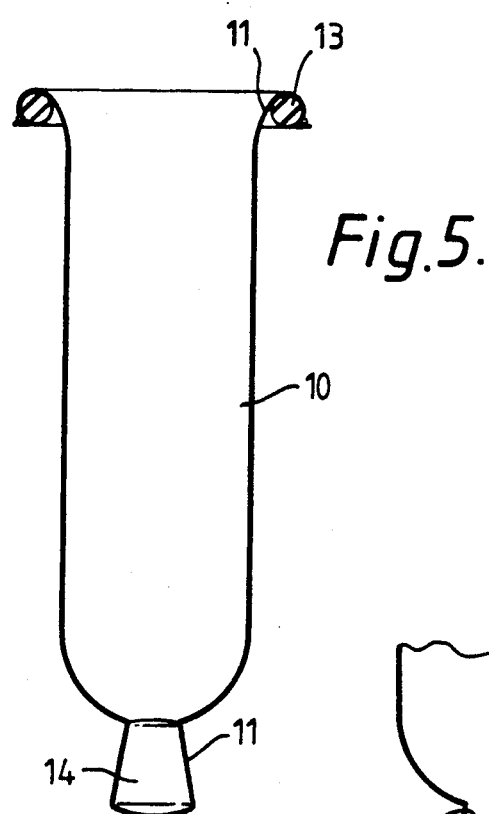
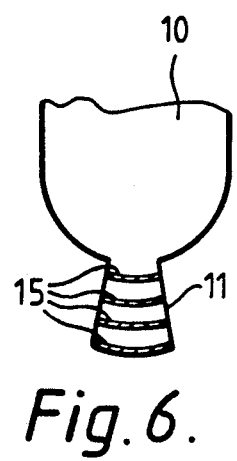

HEALTH CARE DEVICE

This application is a continuation of U.S. patent application Ser. No. 129,736, filed Dec. 7, 1987 now abandoned.

BACKGROUND AND OBJECTS OF THE INVENTION

This invention relates to health care devices and more particularly to such devices made from rubber or rubber composition or other materials having similar composition or characteristics, for use as birth control during sexual intercourse.

The device is intended to provide an effective means of preventing transmission of disease during sexual intercourse.

The device is also intended to provide an exceptionally reliable means of contraception.

To make the use of the health care device more acceptable, means are provided in the invention to replace any loss of, or enhance, sensitivity occasioned by it's use.

According to one aspect of the invention there is provided a device which comprises a sheath having an annular ring of solid but relatively pliable construction attached to the outward open end thereof, such sheath being formed to be inserted within a vaginal or anal body orifice prior to sexual intercourse.

The sheath may have as an integral part of it's construction at the closed end a formed shape intended to locate and maintain the sheath in the body orifice during use. However this member may be provided as a separate part to be inserted at the closed end of the sheath before use.

The locating member or formed shape may be of differing configurations but preferably is frusto-conical, conical, tapered, helical or formed of differing diameter rings and is inserted base first.

The annular ring is preferably of larger diameter than the sheath to reduce genital contact between participating couples, in use thereby to prevent transmission of disease.

In a further embodiment at least one inflatable portion is provided and is intended to be inside the body orifice, in use.

The inflatable portion(s) may be constructed in the wall of the sheath with a ducted connection to an inflator intended to be manually operated.

Alternatively the inflatable portion(s) may be attached or removeably attached to the annular ring and provided with a ducted connection to a manually operated inflator.

In a further embodiment a hollow member may be attached or removeably attached to the annular ring with ducted connection to the inflatable portion(s) to be operated by bodily contact, in use.

The inflatable portion can be of varying forms but is preferably in at least two sections so that in use it will not prevent ejaculation.

BRIEF DESCRIPTION OF THE FIGURES

The foregoing and further features of the invention may be more readily understood from the following description of some preferred embodiments thereof, by way of example, with reference to the accompanying drawings, in which:

FIG. 1 is a side elevational view of a sheath;

FIG. 2 is a side sectional view of an annular ring;

FIG. 3 is a side sectional view of the annular ring of FIG. 2 attached to the sheath of FIG. 1;

FIG. 4 is a side elevational view of a frusto-conical member;

FIG. 5 is a side elevational view of the frusto-conical member of FIG. 4 located within the assembly of FIG. 3;

FIG. 6 is a side elevational view of an alternative arrangement to FIG. 5 at the closed end of the sheath;

BRIEF DESCRIPTION OF PREFERRED EMBODIMENTS

Figure 7:
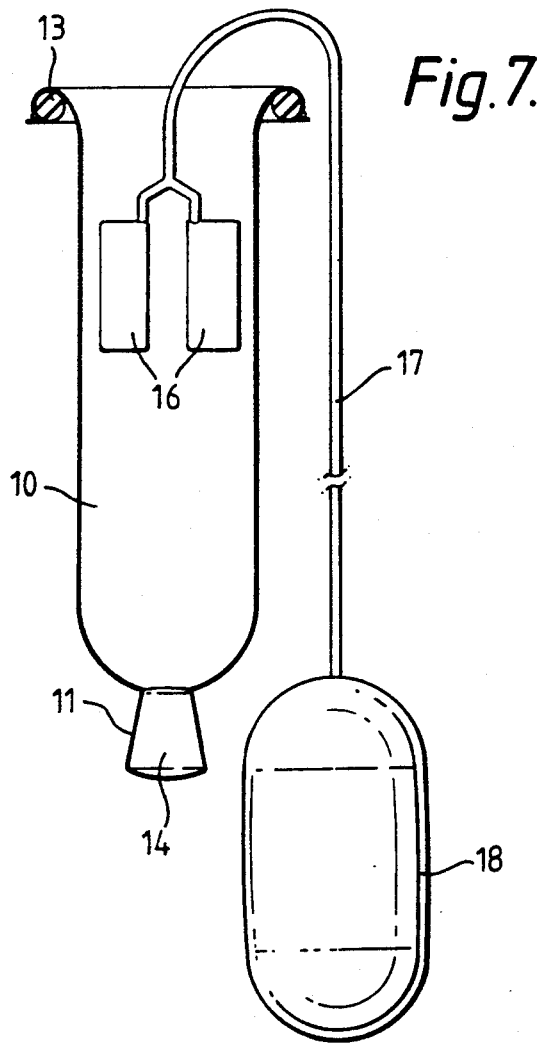
FIG. 7 is a diagrammatic side sectional view of the arrangement of FIG. 5 with an inflatable portion incorporated therein.

Referring now to the drawings FIG. 1 shows a side elevational view of a sheath 10, having an outer open end 11 and a restricted closed end 12, for insertion into a vaginal or anal orifice prior to sexual intercourse. The sheath 10 may be formed from rubber, rubber composition or other suitable material or compositions thereof.

FIG. 2 shows a side sectional view of an annular ring 13 which may be removeably attached, or formed integrally with, the open end 11 of sheath 10 as shown in FIG. 3 and may be formed of similar materials to that of sheath 10.

FIG. 4 is a side elevational view of a frusto-conical locating and retaining member 14 which is formed of a size to locate within restricted portion 12 of sheath 10 prior to use or may be formed integrally with such portion 12. FIG. 5 shows such an arrangement and FIG. 6 shows an alternative arrangement in which member 14 is replaced by a plurality of rings 15 of different diameters formed integrally with portion 11 or may comprise a helical member approximating to rings 15 which may be a separate member.

Since the device is designed to be inserted into a vaginal or anal orifice prior to sexual intercourse it is necessary to provide the annular ring 13 and locating member 14 or 15 to provide positive outer and inner location of the sheath 10 respectively, prior to and during use.

Referring now to FIG. 7 there is shown the arrangement of FIG. 5 but with the incorporation of inflatable portions 16 located in sheath 10. Such portions 16 are connected via ducting 17 to a manually operable inflator 18. This arrangement may be utilised to increase sensitivity or stimulation, during use, which may be decreased by use of the device.

Figure 8:
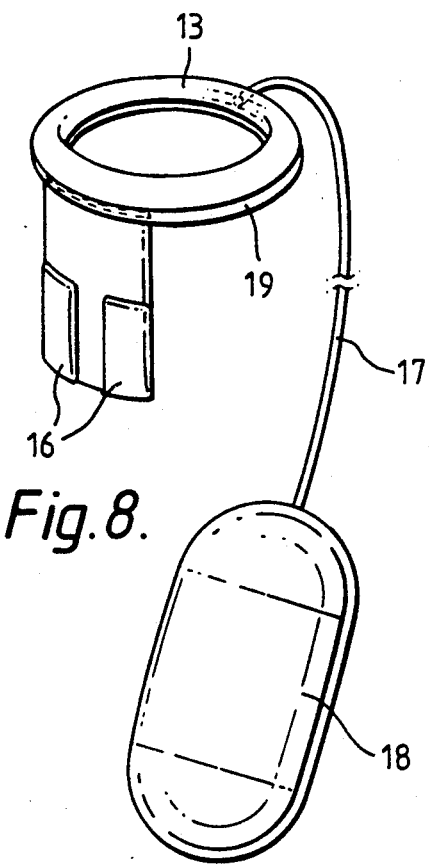
FIGS. 8 and 9 are diagrammatic perspective views of alternative arrangements to that shown in FIG. 7.

FIG. 8 shows an alternative arrangement to that of FIG. 7 in which annular ring 13 includes ducting 19 for connection between ducting 17 and inflatable portions 16 which are attached to annular ring 13.

Figure 9:
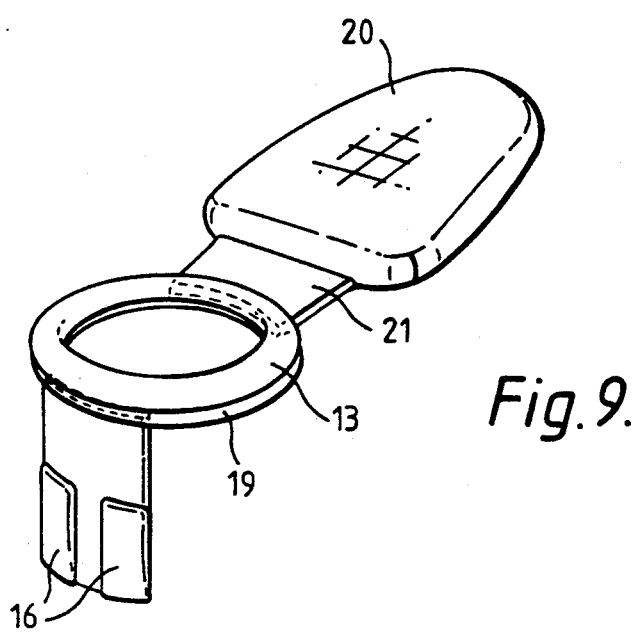

FIG. 9 shows an alternative arrangement to that of FIG. 8 in which the inflator 18 is replaced by a hollow relatively flat cushion member 20 connected by ducting 21 to the ducting 19 of annular ring 13. In the use of this arrangement the bodily contact of the participants provides the inflation of portions 16 and can be increased or decreased by either as required.

Although the major object of the invention is to provide a device to reduce transmission of disease and provide contraceptive protection during sexual intercourse, the device, particularly as shown in FIG. 9, could be utilised to increase sensitivity and stimulation when used in conjunction with a conventional male sheath.

I claim:

1. A prophylactic device comprising:
   a sheath having an outward open end, a closed end, and an outer surface, said closed end defining a restricted portion, and said sheath being so formed to facilitate insertion within a body orifice prior to sexual intercourse;
   outer location means for locating said outward open end outside the body orifice prior to use, said outer location means comprising a pliable annular ring attached to said outward open end of said sheath; and
   inner location and retention means for locating and retaining said sheath within the body orifice during use, said inner location and retention means comprising a separate member located within said restricted portion of said sheath.

2. A device as claimed in claim 1 wherein said separate member is of frusto-conical shape having a top and a base, with said base having a greater diameter than said top, and with said base located toward said closed end of said sheath.

3. A device as claimed in claim 1 wherein said separate member is tapered helical form having a top and a base, with said base having a greater diameter than said top, and with said base located toward said closed end of said sheath.

4. A device as claimed in claim 1 wherein said separate member comprises a formed shape.

5. A device as claimed in claim 1 wherein said annular ring is removably attached to said sheath.

6. A device as claimed in claim 1 wherein said annular ring is of larger diameter than said outer open end of said sheath, to reduce genital contact between participating couples, in use.

7. A device as claimed in claim 1 wherein said annular ring is solid.

8. A prophylactic device comprising:
   a sheath having an outward open end, a closed end, and an outer surface, said closed end defining a restricted portion, and said sheath being so formed to facilitate insertion within a body orifice prior to sexual intercourse;
   outer location means for locating said outward open end outside the body orifice prior to use, said outer location means comprising a pliable annular ring attached to said outward open end of said sheath; and
   inner location and retention means for locating and retaining said sheath within the body orifice during use, said inner location and retention means being formed integrally with said restricted portion of said sheath.

9. A device as claimed in claim 8 wherein said inner location and retention means comprises a plurality of juxtaposed rings of different diameter, the largest diameter of said rings being formed adjacent said closed end of said sheath.

10. A device as claimed in claim 8 wherein said annular ring is removably attached to said sheath.

11. A device as claimed in claim 8 wherein said annular ring is of larger diameter than said outer open end of said sheath, to reduce genital contact between participating couples, in use.

12. A device as claimed in claim 8 wherein said inner location and retention means is of frusto-conical shape having a top and a base, with said base having a greater diameter than said top, and with said base located toward said closed end of said sheath.

13. A device as claimed in claim 8 wherein said inner location and retention means is a tapered helical form having a top and a base, with said base having a greater diameter than said top, and with said base located toward said closed end of said sheath.

14. A device as claimed in claim 8 wherein said annular ring is solid.

* * * * *